(12) United States Patent
Hansen

(10) Patent No.: US 9,874,515 B2
(45) Date of Patent: Jan. 23, 2018

(54) METHOD OF AND APPARATUS FOR CORRECTING FOR INTENSITY DEVIATIONS IN A SPECTROMETER

(71) Applicant: Foss Analytical, Hilleroed (DK)

(72) Inventor: Per Waaben Hansen, Kgs. Lyngby (DK)

(73) Assignee: Foss Analytical A/S, Hilleroed (DK)

( * ) Notice: Subject to any disclaimer, the term of this patent is extended or adjusted under 35 U.S.C. 154(b) by 131 days.

(21) Appl. No.: 14/895,946

(22) PCT Filed: Jun. 4, 2013

(86) PCT No.: PCT/EP2013/061490
§ 371 (c)(1),
(2) Date: Dec. 4, 2015

(87) PCT Pub. No.: WO2014/194935
PCT Pub. Date: Dec. 11, 2014

(65) Prior Publication Data
US 2016/0123870 A1 May 5, 2016

(51) Int. Cl.
*G01N 21/35* (2014.01)
*G01N 21/27* (2006.01)
(Continued)

(52) U.S. Cl.
CPC ............ *G01N 21/35* (2013.01); *G01J 3/0291* (2013.01); *G01J 3/42* (2013.01); *G01J 3/45* (2013.01);
(Continued)

(58) Field of Classification Search
CPC ................. G01N 2201/1285; G01N 2201/128
See application file for complete search history.

(56) References Cited

U.S. PATENT DOCUMENTS

| 5,121,337 A | * | 6/1992 | Brown ................. G01N 21/274 250/339.12 |
| 5,933,792 A | | 8/1999 | Andersen et al. |

(Continued)

FOREIGN PATENT DOCUMENTS

| EP | 2213999 A1 | 8/2010 |
| GB | 2494693 A | 3/2013 |
| WO | WO-2013/026466 A1 | 2/2013 |

OTHER PUBLICATIONS

International Search Report PCT/ISA/210 for International Application No. PCT/EP2013/061490 Dated Mar. 3, 2014.

*Primary Examiner* — Kenneth J Malkowski
(74) *Attorney, Agent, or Firm* — Harness, Dickey & Pierce, P.L.C.

(57) ABSTRACT

A method of determining a pathlength deviation of a sample (610), the method comprising: exposing the sample (610) to electromagnetic radiation at a plurality of wavenumbers, determining electromagnetic absorption in the sample (610) at the plurality of wavenumbers, determining a first wavenumber associated with a first absorption level of an absorption band and a second wavenumber associated with a second absorption level of the absorption band, wherein the second wavenumber is different from the first wavenumber, determining a difference between the first wavenumber and the second wavenumber, and determining the pathlength deviation based on the difference.

18 Claims, 7 Drawing Sheets

(51) Int. Cl.
*G01J 3/02* (2006.01)
*G01J 3/42* (2006.01)
*G01J 3/45* (2006.01)

(52) U.S. Cl.
CPC ... *G01N 21/274* (2013.01); *G01N 2021/3595* (2013.01); *G01N 2201/061* (2013.01); *G01N 2201/12746* (2013.01)

(56) References Cited

U.S. PATENT DOCUMENTS

| | | | |
|---|---|---|---|
| 5,959,738 A | 9/1999 | Hafeman et al. | |
| 6,188,476 B1 | 2/2001 | Hafeman et al. | |
| 6,320,662 B1 | 11/2001 | Hafeman et al. | |
| 6,404,501 B1 | 6/2002 | Hafeman et al. | |
| 6,862,534 B2 * | 3/2005 | Sterling | A61B 5/14532 702/22 |
| 7,009,180 B2 * | 3/2006 | Sterling | A61B 5/14532 250/339.09 |
| 2013/0070236 A1 | 3/2013 | Hulme et al. | |

\* cited by examiner

METHOD OF AND APPARATUS FOR CORRECTING FOR INTENSITY DEVIATIONS IN A SPECTROMETER

CROSS-REFERENCE TO RELATED APPLICATIONS

This application is a national phase under 35 U.S.C. §371 of PCT International Application No. PCT/EP2013/061490 which has an International filing date of Jun. 4, 2013, the entire contents of which are hereby incorporated by reference.

FIELD OF THE INVENTION

The present invention relates to a method for calibrating a spectrometer which determines an electromagnetic spectrum from a sample. More specifically, the present invention relates to a method of correcting for intensity deviations in a spectrometer.

BACKGROUND ART

Within the food industry, e.g. the dairy industry, it is often of vital importance to have knowledge about the characteristics of various food products, such as their chemical composition and their associated concentrations. One method of measuring these characteristics utilizes a spectrometer. The spectrometer typically measures the intensity of electromagnetic radiation which is transmitted through, or reflected by, a sample as a function of a collection of wavenumbers or wavelengths, or a wavenumber band, comprised in a particular region of the electromagnetic spectrum, such as the infrared part of the spectrum. The band wavenumber position may be used to identify the content in a sample by means of its chemical structure.

The food products to be analyzed may be of liquid, solid or gaseous form and held in a sample cuvette for analysis. For example, liquid food products may be milk, wine, cream or yoghurt. Moreover, solid food products may be cheese, meat, grain, etc. If the sample is of liquid or gaseous form, the sample is typically kept in a flow-through cuvette during measurements.

A spectrometer comprises a lot of sensitive optical elements, whereby it needs to undergo a careful calibration procedure before it can be put to use. The sensitive optical elements are exposed to wear and tear of various types, e.g. induced by operation of the spectrometer, well as changing operational conditions, such as changes in the surrounding atmospheric conditions. More specifically, the intensity and the wavelength need to be calibrated before a reliable measurement can be initiated. The measured intensities of two different spectrometers typically differ when analyzing the same sample due to their different background spectra. For example, each background spectrum may comprise information about the electromagnetic source, optical parts in the spectrometer as well as intrinsic detector properties. Thus, the background spectrum needs to be subtracted from the measured spectrum in order to obtain a spectrum which is independent of the particular spectrometer used.

A problem with these spectrometers is that each of them needs to be calibrated, which may be a tedious and time consuming task. Fortunately, methods for standardizing spectrometers have been developed in order to solve this problem. In U.S. Pat. No. 5,933,792 there is disclosed a method for standardizing a spectrometer which generates an optical spectrum from a sample. According to the method, one or several optical spectra of a standardization sample, such as a mixture of water and propanol, are obtained by a spectrometer to be standardized, whereby each optical spectrum shows a characteristic pattern in a predetermined frequency range. These characteristic patterns are then compared to reference patterns which constitute the desired standard responses from the standardization sample. Thereafter, a set of standardizing parameters, describing the transition of the generated characteristic patterns of the spectrometer to be standardized to the reference patterns, are determined and stored. Thereby, according to the method as disclosed in U.S. Pat. No. 5,933,792, calibrations may be transferred between different spectrometers at will. A calibrated spectrometer typically has to be recalibrated at regular time intervals.

However, during operation, the cuvette is often degraded by the sample comprised therein, which causes the calibration to become unstable over time.

SUMMARY OF THE INVENTION

It is therefore an object of the present inventive concept to provide an improved method for correcting for cuvette pathlength deviations.

It is a further object of the present inventive concept to provide an apparatus for implementing this correction.

According to a first aspect of the present inventive concept, there is provided a method for determining a pathlength deviation of a sample. The method comprises: exposing the sample to electromagnetic radiation at a plurality of wavenumbers, determining electromagnetic absorption in the sample at the plurality of wavenumbers, determining a first wavenumber associated with a first absorption level of an absorption band and a second wavenumber associated with a second absorption level of the absorption band, wherein the second wavenumber is different from the first wavenumber, determining a difference between the first wavenumber and the second wavenumber, and determining the pathlength deviation based on the difference.

A radiation device may be arranged to expose the sample to electromagnetic radiation, which after transmission may be detected by a detector. The detector may be arranged to detect the intensity of a received electromagnetic radiation at different wavenumbers. By pathlength, or sample pathlength, is meant a distance that the electromagnetic radiation passes through the sample. The pathlength may be regarded as a thickness of the sample in a direction which is parallel to the direction of the electromagnetic radiation sent through the sample. If the sample is kept in a sample cuvette, the sample pathlength will coincide with an inner cuvette length extension. The inner cuvette length extension is typically considered a length extension between inner walls of the cuvette. Therefore, the terms cuvette pathlength and sample pathlength may be used interchangeably. Of course, since the inner cuvette length extension may vary along its inner walls, also the sample pathlength may vary accordingly. In a non-limiting example, a typical cuvette pathlength has an extension between 30 micrometers to 60 micrometers.

By a pathlength deviation is meant a deviation from a nominal value, or a reference value, of the pathlength. For example, the reference value of the pathlength may be a pathlength at a particular time instant. In a non-limiting example, a typical pathlength deviation to be determined by the inventive method lies between 1 and 5 micrometers. It is understood that once a pathlength deviation is determined, the pathlength may also be determined by adding or subtracting the pathlength deviation to a reference value of the pathlength. It is noted that according to an alternative embodiment, the inventive method may be used for determining an absolute value of the pathlength of a sample by relating it to the difference.

The first and second wavenumbers may correspond to an electromagnetic radiation absorption band of a reference liquid, or at least a component of the reference liquid. Preferably, this liquid presents substantial absorption in a well-defined range of wavenumbers. Examples of reference liquids include water and mineral oils.

Clearly, instead of expressing the spectral information about the electromagnetic radiation in terms of a wavenumber, one may instead use a wavelength or a frequency. Furthermore, the plurality of wavenumbers may be a discrete collection of wavenumbers, or alternatively, a continuous set of wavenumbers. Preferably, the electromagnetic radiation is polychromatic, but also monochromatic radiation is equally conceivable. It is also understood that instead of determining electromagnetic absorption in the sample, an electromagnetic intensity or transmission may equally well be determined.

In accordance with the inventive concept, the pathlength deviation of the sample may be determined based on the difference between the first wavenumber and the second wavenumber, which means that when the present method is applicable, the method as prescribed in U.S. Pat. No. 5,933,792 may become redundant. More specifically, in order to correct a pathlength deviation, there is no need for utilizing a standardization sample, such as a mixture of water and propanol. Thus the inventive concept may be advantageous when the standardization sample is difficult to introduce to the spectrometer. This may happen when the spectrometer is part of an in-line process and is hard to access.

In addition, there is no need of comparing the characteristic pattern of the measured spectrum with a reference pattern. Thus, there is provided an improved method for correcting for cuvette pathlength deviations. In view of the Beer-Lambert law, which describes a relation between the measured intensity and the pathlength, also intensity deviations, or alternatively absorbance deviations, may therefore be corrected by the inventive concept.

In certain circumstances, it may be difficult or impossible to measure the intensity of a certain chemical functional group, due to substantial absorption in a specific wavenumber range. Nevertheless, by means of the inventive method, the width of this range may still be determined, which in turn may be related to the pathlength deviation. Thus, the pathlength deviation may be determined, to a certain degree of accuracy, even in wavenumber regions where substantial absorption is present, where the intensity signal may be substantially saturated (or below the noise floor depending on how the measurement is performed).

An additional advantage of the present inventive concept is that there is provided a method for detecting the pathlength deviation based on an individual spectrum of a sample, e.g. a reference fluid.

Yet another advantage of the present inventive concept is that there is no need for expertise in the art of handling the standardization sample. Also, the inventive method may be applied in operational environments which are less standardized. For instance, there may be weaker requirements on an allowed set of operational temperatures of the spectrometer.

Optionally, the pathlength deviation may be determined by determining a plurality of absorption levels and a plurality of associated wavenumbers.

According to one embodiment, the electromagnetic radiation is infrared radiation. In this case, the spectral region to be analyzed concerns the infrared spectrum, i.e. wavenumbers ranging from approximately 14 000 $cm^{-1}$ to 10 $cm^{-1}$, corresponding to wavelengths ranging from 700 nanometer to 1 millimeter, respectively. In particular, mid-infrared radiation with wavelengths from 3 to 10 micrometers may be used. An advantage of using infrared radiation is that infrared spectroscopy is simple and reliable. In addition, most organic components absorb in the infrared part of the spectrum. According to one embodiment, the absorption is determined by Fourier transform spectroscopy. In the case of IR spectroscopy, a Fourier transform infrared (FTIR) spectrometer may be used. According to alternative embodiments, the absorption is determined by other types of spectroscopy, such as dispersive spectroscopy.

According to one embodiment, the first and second absorption levels are the same. The first and second absorption levels may be the same up to some predetermined level of accuracy.

According to one embodiment, the first and second wavenumbers correspond to positions on the slopes of an electromagnetic radiation absorption band of water. Here, the sample may comprise water, preferably in liquid form. In one example, the entire sample consists of water. In another example, only a part of the sample comprises water. The absorption band of water used may be the spectral band centred at the wavenumber 1640 $cm^{-1}$, which is related to the O—H bending vibration of water. However, also other absorption bands of water are conceivable. The first and second wavelengths may correspond to the endpoints of the water band. An advantage of this embodiment is that water is easily accessible in a typical operational surrounding in which the inventive method may be applied. For example, when using mid-infrared spectroscopy for measuring liquids, such as milk and wine, water is generally introduced into the cuvette when performing reference measurements. This is to be contrasted with the introduction of the standardization sample as described above in the prior art which typically comprises a very specific type of liquid, which is an extra component needed for standardizing the spectrometers, and which may not be easily accessible to a user of an apparatus which is to be calibrated. Thus, potential cuvette pathlength deviations may be corrected solely based on information from the water spectrum. Another advantage of this embodiment is that water is pure, or at least may be easily purified.

According to one embodiment, the method further comprises the act of estimating a background spectrum by determining a third wavenumber associated with a third absorption level and a fourth wavenumber associated with a fourth absorption level. The third and the fourth absorption level may be located at, or in the proximity of, a maximum in a plot with wavenumber on the horizontal axis and intensity on the vertical axis. The estimated background spectrum may be regarded as sufficiently close to a true background spectrum if a set of predetermined criteria are fulfilled. By means of the background spectrum, a raw, uncorrected detector spectrum, e.g. a single-beam spectrum, may be normalized.

According an alternative embodiment, the background spectrum may be determined using an air measurement, i.e. a measurement in which the cuvette only comprises air. In this case, the sample is absent during the spectral analysis, and a single-beam spectrum comprises information only about the sample cuvette, the air within the cuvette, reflection of mirrors, emission spectrum of the electromagnetic source, the sensitivity of the detector, etc. In this case, a Michelson interferometer, comprising a beam splitter, a stationary mirror and a movable mirror, may be utilized.

According to one embodiment, the estimating comprises the act of expressing the background spectrum as a polynomial of order N, using the determined the third and fourth wavenumbers and the third and fourth absorption levels. N may be any natural integer. For uniqueness, N+1 constants need to be specified for a polynomial of order N. Thereby, N+1 pairs of numbers $(k_n, A_n)$, n=0, 1, 2, . . . , N, need to be specified, where $A_n$ is the absorbance at wavenumber $k_n$. According to yet an alternative embodiment, the estimating comprises the act of expressing the background spectrum as a mathematical function of one variable.

According to one embodiment, the act of determining the pathlength deviation is implemented by assuming a linear relationship between the pathlength deviation and the difference D between two wavenumbers. By means of this assumption, two parameters, say a and b, describing a slope and an intercept, respectively, have to be fixed. The linear relation is assumed to be approximately true at least within a specific range of wavenumbers and pathlengths. In this range, the parameters a and b are constant. The parameters a and b may be fixed once and for all for a specific spectrometer. For example, a and b may be determined by correlating the difference D with the pathlength established from the method of U.S. Pat. No. 5,993,792. Alternatively, a and b may vary with time. For instance, a and b may be continuously updated each time a calibration of the spectrometer is performed.

According to one embodiment the determined pathlength deviation is used for detecting air in the sample. The air may be in the form of air bubbles which effectively dilutes the concentration of the material associated with the absorption band on which the measurements are made. An advantage of this embodiment is that, since the pathlength appears to be smaller in the presence of air, the signs of air in the sample are different from normal wear, which actually causes an increase in pathlength, of the cuvette which retains the sample. Thus, the apparent pathlength deviation is a clear indication of air in the sample or cuvette, and the air may be removed.

According to a second aspect of the invention, there is provided an apparatus for determining a pathlength deviation of a sample. The apparatus comprises a radiation device arranged to expose the sample to electromagnetic radiation at a plurality of wavenumbers, and a measuring device. The measuring device is arranged to determine electromagnetic absorption in the sample at the plurality of wavenumbers, determine a first wavenumber associated with a first absorption level of an absorption band and a second wavenumber associated with a second absorption level of the absorption band, wherein the second wavenumber is different from the first wavenumber, determine a difference between the first wavenumber and the second wavenumber, and determine the pathlength deviation based on the difference.

The details and advantages of the second aspect of the invention are largely analogous to those of the first aspect of the invention, wherein reference is made to the above. In addition, it is noted that according to one embodiment the sample is placed within the apparatus. According to another embodiment the sample is placed externally to the apparatus.

Generally, all terms used in the claims are to be interpreted according to their ordinary meaning in the technical field, unless explicitly defined otherwise herein. All references to "a/an/the [element, device, component, means, step, etc]" are to be interpreted openly as referring to at least one instance of said element, device, component, means, step, etc., unless explicitly stated otherwise.

BRIEF DESCRIPTION OF THE DRAWINGS

The above, as well as additional objects, features and advantages of the present invention, will be better understood through the following illustrative and non-limiting detailed description of preferred embodiments of the present invention, with reference to the appended drawings, where the same reference numerals will be used for similar elements, wherein.

DETAILED DESCRIPTION OF PREFERRED EMBODIMENTS

Figure 1:
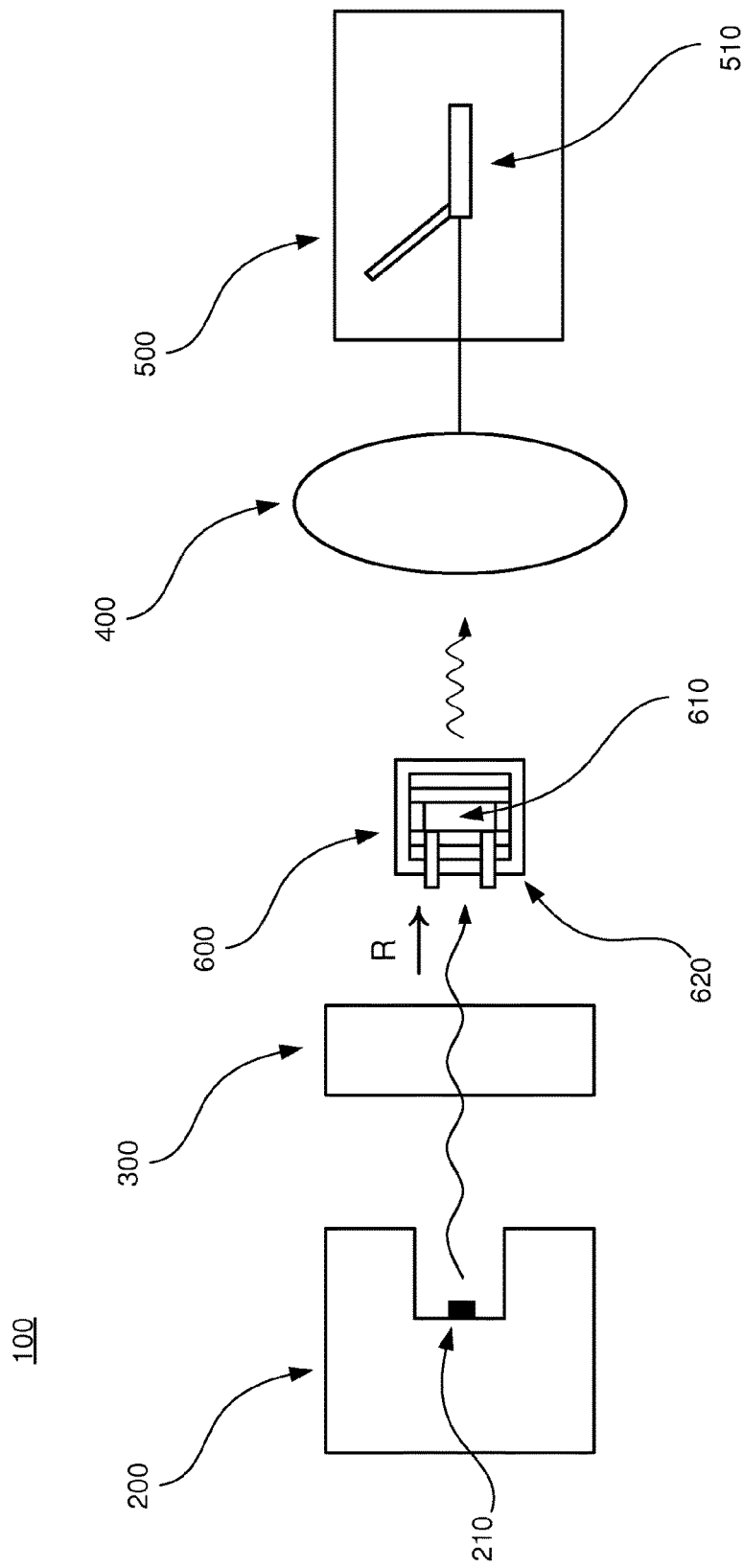
FIG. 1 schematically illustrates an embodiment of the inventive apparatus comprising a sample arrangement which is to be analyzed.

In the following, an embodiment of the inventive apparatus 100 will be described with reference to FIGS. 1 and 2 in the context of absorption spectroscopy. The apparatus 100 comprises a radiation device 200, an interferometric arrangement 300, a detector 400 and a measuring device 500. Also, a sample arrangement 600 to be analyzed is arranged to be placed in the apparatus 100.

Figure 2:
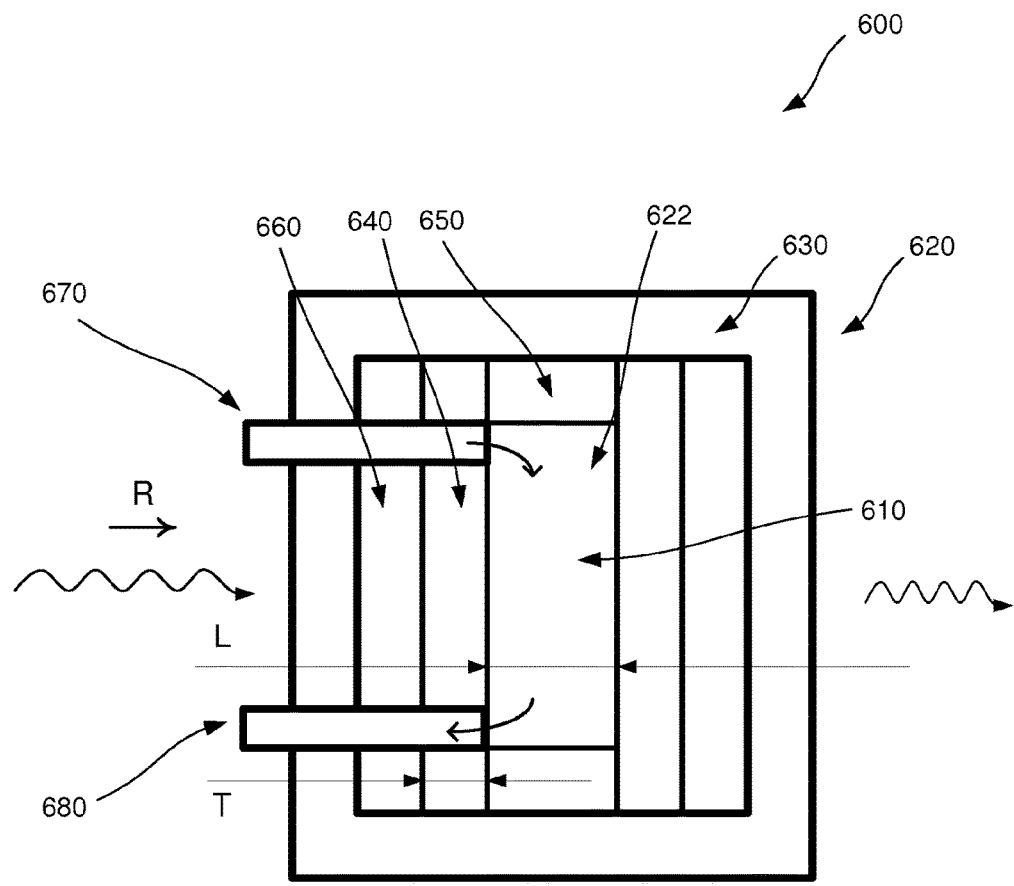
FIG. 2 is a schematic cross-sectional top view of the sample arrangement shown in FIG. 1.

The radiation device 200 comprises a radiation source 210 which is arranged to emit polychromatic infrared radiation in the direction as indicated by the letter R in FIGS. 1 and 2.

The interferometric arrangement 300 comprises necessary equipment for implementing Fourier transform spectroscopy, as is well-known to a person skilled in the art. For example, the interferometric arrangement 300 comprises a collimator which collimates the infrared radiation and additional equipment comprised in an interferometer, e.g optical components such as mirrors and lenses.

The detector 400 is arranged to detect incoming infrared radiation which is transmitted through the sample arrangement 600, see further below.

The measuring device 500 comprises a computer 510 which is connected to the detector 400 for collecting unprocessed data about the detected infrared radiation. By means of this connection, the measuring device 500 is arranged to determine a transmittance in a discrete number of channels positioned equidistantly along a wavenumber axis. The computer 510 comprises a processor for processing the collected data, suitable computing software, as well as additional equipment well-known to a person skilled in the art. Moreover, the computer 510 is arranged to store the collected data and the processed data in a memory. According to the present embodiment, a routine using Fourier transform algorithms is used in order to transform the unprocessed data from the detector 400 into data about the intensity as a function of the wavenumber. Moreover, the computer 510 is arranged to present the data graphically in terms of two-dimensional plots, see FIGS. 5-7 below.

The radiation device 200, the interferometric arrangement 300, the detector 400 and the measuring device 500 will in the following be referred to as a FTIR spectrometer, or simply a spectrometer. Further below, a method for correcting intensity deviations of this FTIR spectrometer will be described.

The sample arrangement 600 is placed between the interferometric arrangement 300 and the detector 400. Furthermore, the sample arrangement 600 is arranged to hold a liquid sample which is to be spectrally analyzed by letting infrared radiation be transmitted through it. For instance, the liquid sample may be milk or wine. In the present embodiment, the liquid sample comprises water 610 which serves as a reference fluid and is used in order to perform corrections of cuvette pathlength deviations, see further below. The water sample 610 is placed in a cuvette 620 which is in part made out of calcium fluoride. The outer surface of the cuvette 620 is shaped as a rectangular parallelepiped. The cuvette 620 comprises inner walls 630, window elements 640, spacers 650, cavities 660 and a sample space 622 for holding the sample 610, see the cross-sectional top view in FIG. 2. It is clear that the inner walls 630 and the window elements 640 are transparent to the infrared radiation which is sent through the sample 610. It is noted that the spacers 650 do not need to be transparent. For example, the spacers 650 may be comprised out of a plastic. The volume of the sample space 622 may be varied by varying the extension of the spacers 650. Indeed, the spacers 650 create a pathlength of the cuvette 620. Furthermore, there is an inlet 670 for introducing the sample 610 into the sample space 622 and an outlet 680 for removing the sample 610 from the space 622. According to the present embodiment, the sample 610 is kept in motion during the measurement, flowing from the inlet 670 to the outlet 680 via the sample space 622, as indicated by the arrows in FIG. 2. According to an alternative embodiment, however, the sample 610 is kept stationary in the sample space 622 during the measurement. The sample 610 is placed in an environment having room temperature. The temperature of the sample is substantially fixed during the spectral analysis.

The distance covered by the infrared radiation in the sample space 622 is referred to as a pathlength. Since the radiation is transmitted through the sample 610 at right angles with respect to a side edge of the cuvette 620, in the direction R in FIG. 1 and FIG. 2, the pathlength L coincides with an inner length extension of the cuvette 620, between the window elements 640. If the cuvette 620 wears down, the pathlength L will change (increase).

In fact, since the window elements 640 making contact with the water sample 610 are made from calcium fluoride, they will be dissolved over time. During its lifetime, the cuvette 620 may also have been deteriorated by other chemicals. For example, the thickness T (see FIG. 2) of the window elements 640 will become smaller over time. Consequently, the pathlength L will increase over time, giving rise to pathlength deviations. In addition, it is noted that cuvettes placed in different apparatuses of the type 100 generically have different pathlengths. For instance, differing pathlengths may have resulted from having dissolved the cuvettes to various degrees, even if the cuvettes have been substantially similar at some point in time. Moreover, the extension of the spacers 650 may vary between different cuvettes 620, thereby giving rise to varying pathlengths. Therefore, in order to make the characteristics of different apparatuses 100 more similar, the vararation of pathlengths need to be compensated for.

Figure 3:
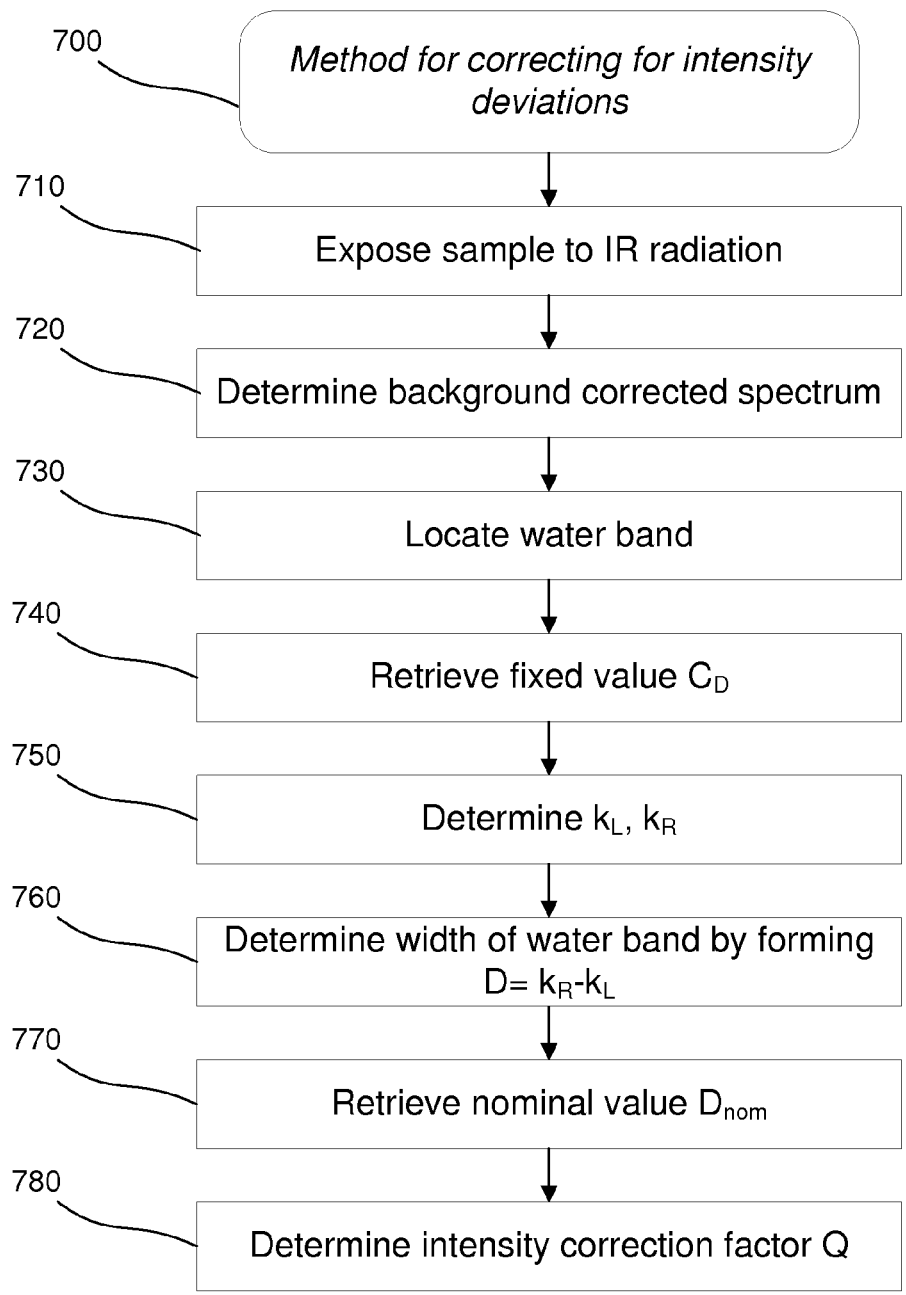
FIG. 3 is a block diagram illustrating a method to correct the intensity deviations according to one embodiment.
Figure 4:
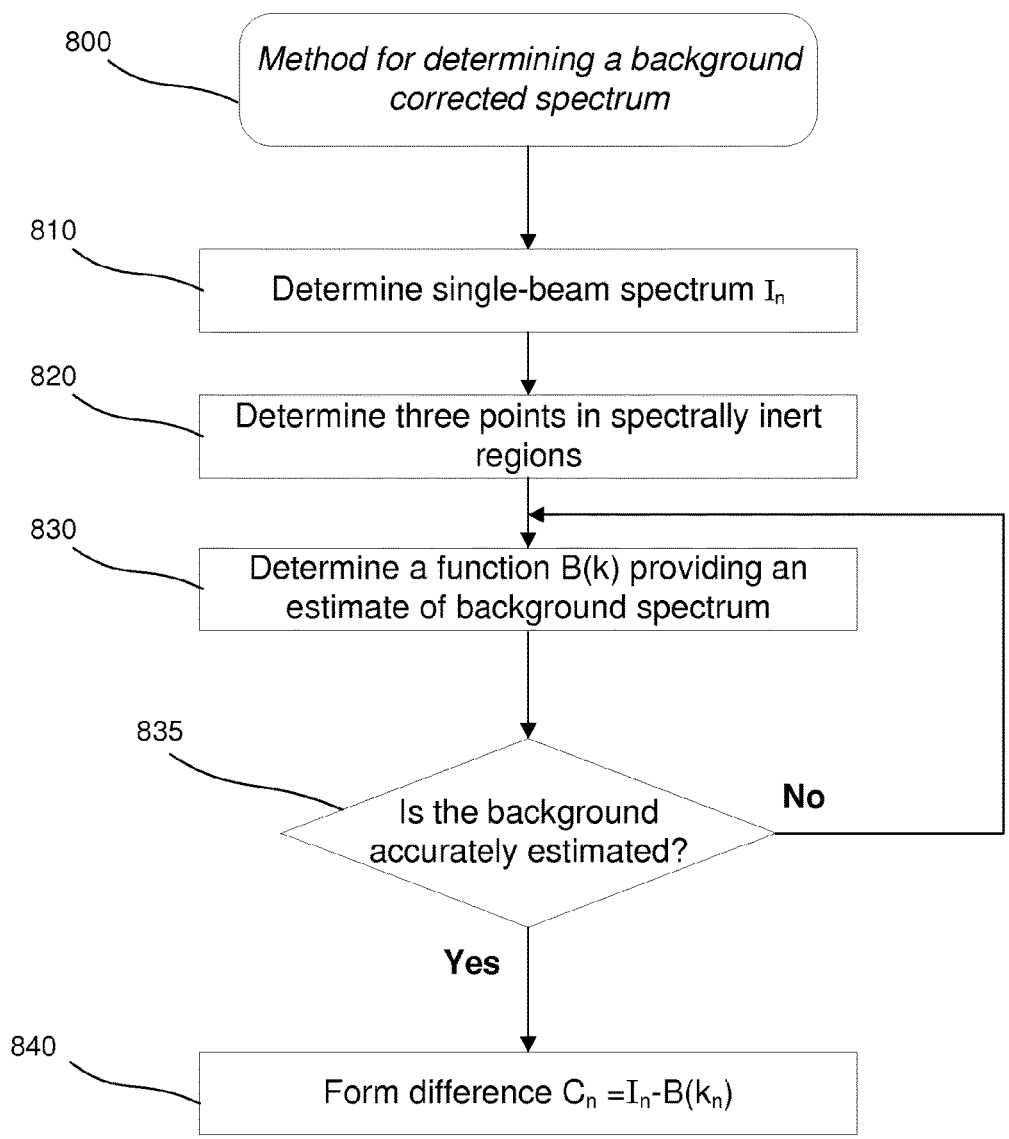
FIG. 4 is a block diagram illustrating a method for determining a background corrected spectrum according to one embodiment.
Figure 5:
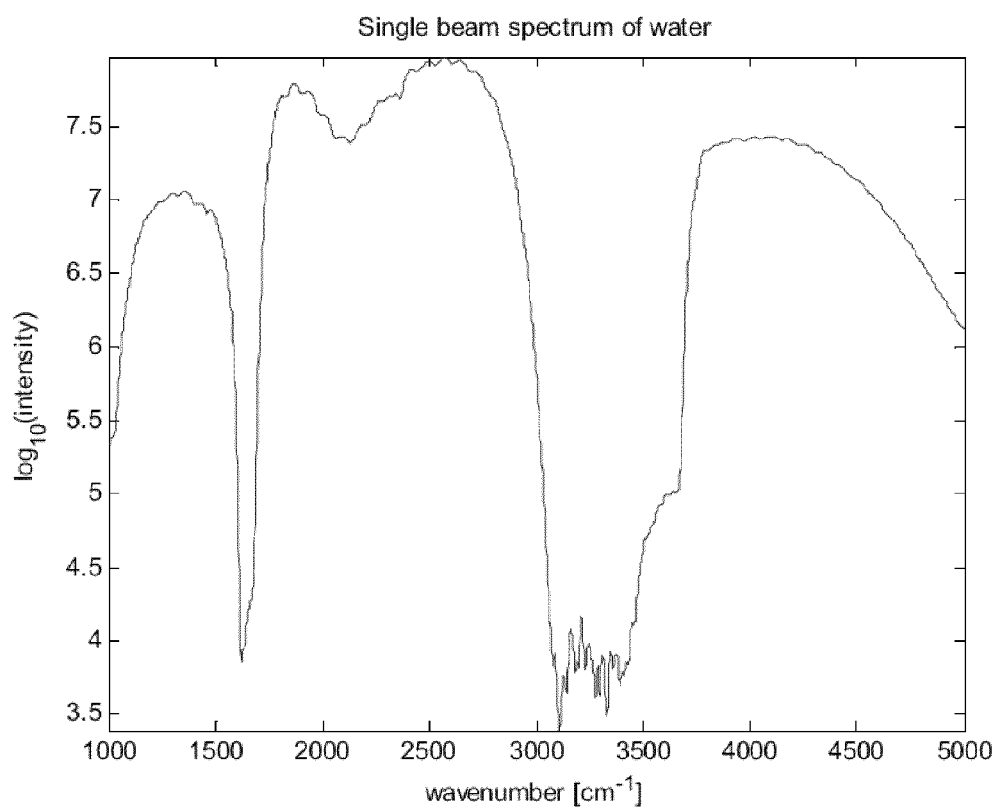
FIG. 5 is a graphical presentation of a single-beam spectrum of water, wherein $\log_{10}$-transformed intensity is plotted versus wavenumber.
Figure 6:
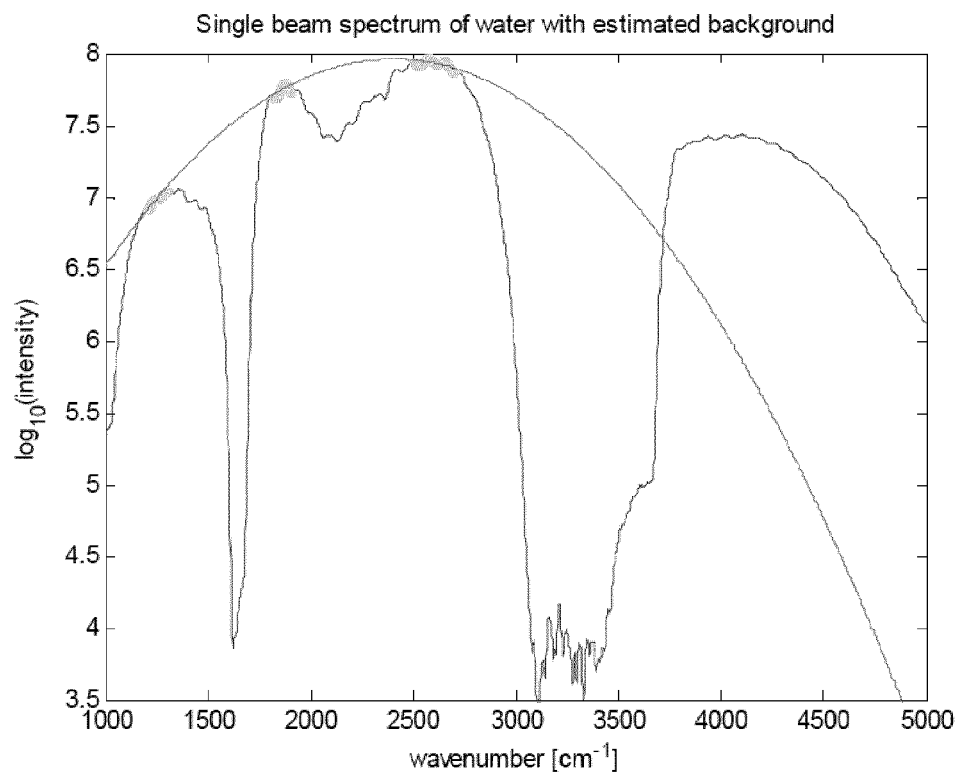
FIG. 6 is a graphical presentation of the single-beam spectrum of water according to FIG. 5 together with an estimated background spectrum.
Figure 7:
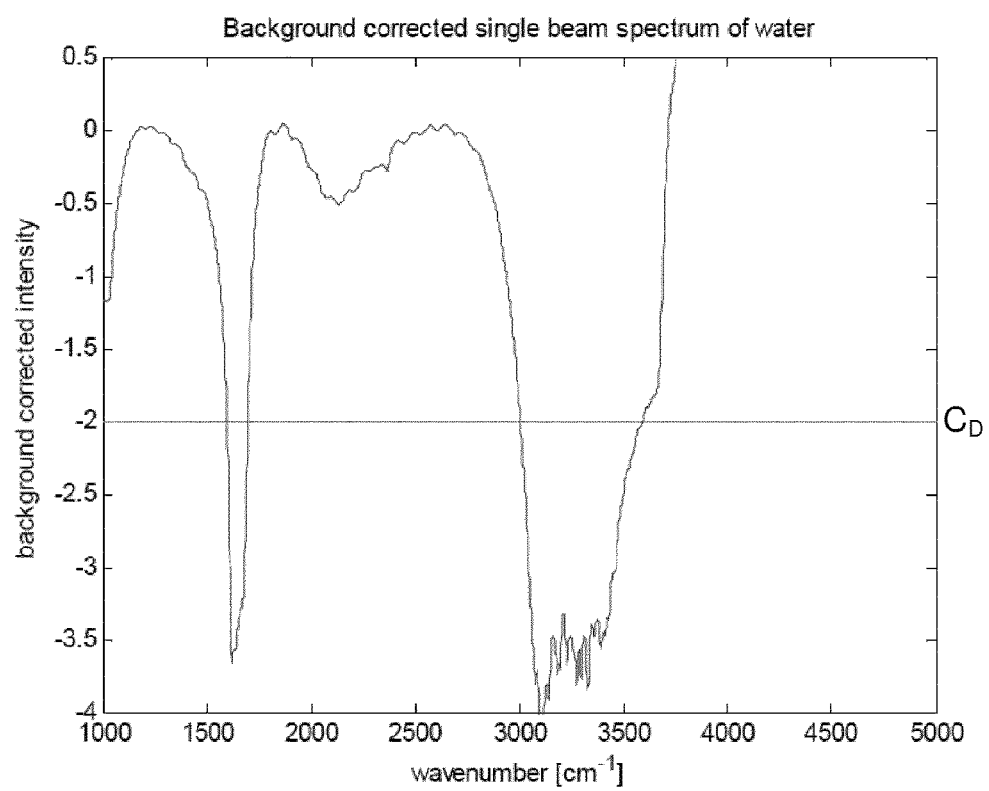
FIG. 7 is a graphical presentation of a background corrected spectrum following from the spectra presented in FIG. 6.

With reference to the block diagrams in FIGS. 3 and 4 and the plots in FIGS. 5-7, the method for correcting intensity deviations in the FTIR spectrometer will now be described. FIGS. 5-7 illustrate various spectra in an example relating to a spectral analysis using a specific cuvette. As will be understood further below, a correction of a pathlength deviation also means a correction of an intensity deviation. According to the present exemplary embodiment the method utilizes the spectrum of water for detecting deviations in cuvette pathlengths. It will however be appreciated that other absorption bands in a sample may be utilized provided that preferably the concentration of the material in that sample causing the absorption band is constant between measurements or at least known so that variations in intensity due to any change in concentration between samples may be taken into account in the correction for pathlength deviation according to the present invention. After the spectrometer has been corrected using the measurements on the water sample, it may be used for measurements on other liquid samples, such as milk or wine.

The method (Box 700) comprises an exposure of the water sample 610 to polychromatic infrared radiation (Box 710) from the radiation device 200. The radiation is illustrated by wavy lines in FIG. 1 and FIG. 2. The detector 400 detects the incoming infrared radiation which has been transmitted through the interferometric arrangement 300, the water sample 610 as well as the cuvette 620, thereby determining (Box 720) the intensity levels for wavenumbers in the range between 1000 $cm^{-1}$ and 5000 $cm^{-1}$, utilizing the measuring device 500. More specifically, the intensity levels for a discrete set of equidistantly distributed wavenumbers $k_n$ in this range are determined, where n=1, 2 . . . , N. In detail, the formula $k_n=1000+4000\cdot(n-1)/(N-1)$ may be used for the distribution of the wavenumbers. For example N=2000, but other values of N are equally conceivable. Preferably, the wavenumbers $k_n$ are equally spaced since a Fourier transform algorithm is used. The intensity data and wavenumber data are stored in the memory of the computer 510.

The resulting $\log_{10}$-transformed intensity levels $I_n$ are plotted in FIG. 5 versus the wavenumbers $k_n$. A log-transformed intensity level will interchangeably be referred to as an intensity level. The spectrum in FIG. 5, manifested as an interpolating curve in a two-dimensional plot, with intensity on the vertical axis and a corresponding wavenumber on the horizontal spectral axis, is termed a single-beam spectrum. According to an alternatively graphical presentation, the plot may be a scatter plot.

It is assumed that the spectral axis has been calibrated, or corrected, to a desired degree of accuracy. In particular, the spectral axis of the spectrometer may be calibrated by a method which is devoid of a standardization sample.

Next, the single-beam spectrum needs to be corrected due to the background and disturbances present in the optical path of the infrared radiation sent out from the radiation device 200. For instance, properties of the source 210, the interferometric arrangement 300, the detector 400 and the cuvette 620 may influence the background spectrum.

The method of determining a background corrected spectrum (Box 800) is now explained in more detail according to the present embodiment with reference to FIG. 4 and FIGS. 5-7.

Once the single-beam spectrum is determined (Box 810) as described above, three regions throughout the curve in FIG. 5 are determined (Box 820) in spectrally inert regions of $I_n$. By a spectrally inert region is in the present context meant a region in which absorption due to the presence of water is low or essentially absent. The three inert regions are indicated in FIG. 6 by thickened areas. The method of determining the three points along the curve is implemented automatically by a subroutine in the computer 510 and the points are stored in its memory. The points in these three regions are labelled by the pair of numbers (k', I'), (k", I") and (k''', I'''), corresponding to the location of the points in the inert regions on the horizontal and vertical axes, respectively, in FIG. 6. k', I', k", I", k''' and I''' may be scalars or vectors, depending on how many points that are chosen within each region. The wavenumbers k', k", and k''' are chosen from the set $k_n$, and the intensities I', I", and I''' are chosen from the set $I_n$, where n=1, . . . , N. According to the present embodiment, any pairs (k', I'), (k", I") and (k''', I''') within the respective thickened areas in FIG. 6 may be used to represent the points. According to alternative embodiments, however, the pairs are acceptable only of they fulfil certain criteria. One of these criteria may be that the each of the points (k', I'), (k", I") and (k''', I''') must be located sufficiently close to a maximum of an interpolating curve which connects the points In.

In the present example, only one point from each region is chosen. According to an alternative embodiment, a plurality of points in each spectrally inert region is used for estimating the background spectrum. In a non-limiting one example, 20 points are used in each region. The plurality of points may be used to determine the background spectrum, e.g. by means of a best fit approximation scheme, such as the least square method.

In order to estimate the background spectrum in terms of a continuous function B(k), with background intensity as a function of a wavenumber k, the following ansatz is made:

$$B(k)=\alpha+\beta \cdot k+\gamma \cdot k^2.$$

Notice that according to the present embodiment, the estimated background spectrum is log-transformed. Thus, the background spectrum is simulated by a second-order polynomial for which three coefficients α, β and γ has to be determined. The coefficients are determined by requiring B(k')=I', B(k")=I" and B(k''')=I'''. The resulting estimated background spectrum, given in terms of the function B(k) (Box 830), is plotted in FIG. 6 in conjunction with the single-beam spectrum. Information related to the function B(k) is stored in the memory of the computer 510.

It is noted that the polynomial may be determined by using other curve-fitting approximation techniques. For example, a best fit approximation scheme may be used. In addition, a polynomial of a different degree may be used. Also, a different number of regions may be used.

Hence, the continuous function B(k) assigns a set of points $(k_n, B_n)$, n=1, . . . N, according to the relation $B_n=B(k_n)$, wherein $B_n$ represents the estimated background spectrum at the wavenumber $k_n$.

Next, a test routine is performed (Box 835) by the computer 510 in order to ensure that the estimated background spectrum is sufficiently accurate according to a predetermined set of conditions. If the conditions are not fulfilled, the procedure of finding an estimated background spectrum may be reiterated. For example, a different type of polynomial degree may be used.

The background corrected spectrum is then finally determined (Box 840) by a subroutine in the computer 510 by forming the difference $C_n=I_n-B_n$. The discrete function $C_n$ is plotted in FIG. 7 versus the wavenumbers $k_n$. Note that $C_{k'}=C_{k''}=C_{k'''}=0$, which may be interpreted as the absorbance being estimated to be zero at these wavenumbers. Information related to the function $C_n$ is stored in the memory of the computer 510.

According to alternative embodiments, other methods of determining the background corrected spectrum may be used. For example, a continuous interpolating function $I^{sb}(k)$ may be used to represent the single-beam spectrum instead of the discrete set $I_n$. The pairs of numbers $(k_n, I_n)$ for n=1, . . . , N may determine a function $I^{sb}(k)$ for the single-beam spectrum in terms of the wavenumber k. $I^{sb}(k)$ may be determined by a subroutine in the computer 510 and may be stored in its memory. In one example the function $I^{sb}(k)$ is a piecewise linear interpolating function and passes through all the points $(k_n, I_n)$. In another example, the function $I^{sb}(k)$ is a smooth function which is determined from best-fit techniques using the data set $(k_n, I_n)$. In the latter case, the function is required to pass $I^{sb}(k)$ sufficiently close to the points $(k_n, I_n)$ according to a predetermined level of accuracy. It is understood that other methods of determining $I^{sb}(k)$ are equally conceivable. Using the function $I^{sb}(k)$, the background corrected spectrum may be expressed as a continuous function $C(k)=I^{sb}(k)-B(k)$.

Once a background corrected spectrum is determined, a subroutine is initiated by the computer 510 to locate the water band centered around the wavenumber 1640 cm$^{-1}$ (Box 730). In this step, the background corrected data is analyzed. Alternatively, the subroutine may be manual, e.g. performed by inspecting the background corrected spectrum visually. In FIG. 7, the water band is identified as the valley located around wavenumber 1640 cm$^{-1}$. This water band is related to the O—H bending vibration of water. Information about the location of the water band is stored in the memory of the computer 510.

Optionally, the background corrected spectrum may be further corrected by taking into account variations due to external quantities, such as temperature, air humidity, and air pressure. In one example, variations of at least one of these quantities are induced during one or several measurements on the sample and needs to be corrected. In another example, the spectrum obtained at a first external quantity is transformed to a spectrum which is valid at a second external quantity.

According to the Beer-Lambert law, the log-transformed intensity is linearly proportional to the concentration of water as well as the sample pathlength. More specifically, the absorbance $A=\log_{10}(I_0/I)$ under suitable conditions approximately fulfils the relation $A=\epsilon \cdot c \cdot L$, where $\epsilon$ is the molar absorbtivity, c is the concentration of material in the sample causing the so monitored absorption and L is the pathlength. Here, $I_0$ is an intensity of electromagnetic radiation through a reference cell and I is an intensity of electromagnetic radiation after being transmitted through the sample. Since the concentration c of water is constant (in a water sample), the intensity is linearly correlated to the pathlength. It will be appreciated that this linear correlation will exist for any absorption band monitored in a method according to the present invention provided that the concentration of the material in the sample causing the absorption remains constant between samples and between measurements. In the case of water, it is difficult, or even impossible, to measure the intensity of the water band at wavenumber 1640 cm$^{-1}$, since the absorption of water at the cuvette pathlength typically used is substantial and the signal therefore becomes saturated or at least becomes close to being saturated.

Nevertheless, the inventor has found that a change in the pathlength not only affects the intensity of the relevant absorption band (in the present embodiment a water absorption band) but also its width. In fact, a relation between the width of the absorption (here a water absorption) band and the pathlength deviation may be established as will be explained in further detail below.

In order to determine the width of the water band, a fixed value $C_D$ of the background corrected intensity is determined. For example, $C_D$ may be retrieved (Box 740) from a database which is stored in the computer 510 memory. More specifically, the width of the water band is to be determined at the intensity $C_D$. The value is chosen so that the line $C=C_D$ intersects the water band at a predetermined distance from the minimum of the valley. At the minimum of the valley, there is typically a substantial amount of noise (not seen in FIG. 7) which may prevent a sufficiently accurate determination of the width. The predetermined distance may be fixed from a set of requirements. Alternatively, the predetermined distance may be chosen from a list of fixed numbers which are stored in memory of the computer 510. In the present example, the value $C_D=-2$ is chosen and the line $C=C_D$ is plotted in FIG. 7.

The line $C=C_D$ intersects the background corrected intensity $C_n$ at the wavenumbers $k_L$ and $k_R$, see FIG. 7. The left and right wavenumbers $k_L$ and $k_R$ are determined (Box 750) and, subsequently, the water band width is determined by forming the difference $D=k_R-k_L$ (Box 760). The determinations are established by subroutines implemented in the computer 510. Information about $k_L$, $k_R$ and D is stored in the memory of the computer 510. In the example currently under consideration, with the spectrum as given in FIG. 7, it is established that $k_L=1594.70$ cm$^{-1}$, $k_R=1695.82$ cm$^{-1}$ and $D=101.12$ cm$^{-1}$.

Note that the continuous line $C=C_D$ typically does not intersect a specific discrete $C_n$ value, wherefore an approximation scheme needs to be adopted which is well-known by a person skilled in the art. For example, if the line $C=C_D$ approximately passes through an intensity lying between $C_m$ and $C_{m+1}$, at a value of the wavenumber lying between $k_m$ and $k_{m+1}$, the intensity values for wavenumbers in between $k_m$ and $k_{m+1}$ may be approximated by a straight line $C_{line}(k)$ which fulfils $C_{line}(k_m)=C_m$ and $C_{line}(k_{m+1})=C_{m+1}$. On the contrary, if the continuous function $C(k)$ is used to represent the background corrected spectrum, the values of k for which the line $C=C_D$ intersects $C(k)$ are unique. Next, a nominal value $D_{nom}$ for the water band width is determined. For example, $D_{nom}$ may be retrieved (Box 770) from a database stored in the computer. The nominal value $D_{nom}$ may be fixed by calculating the average water band width of a plurality of cuvettes. In the present example, it is found that $D_{nom}=105.31$ cm$^{-1}$. It is noted, however, that any other nominal value may be used. The nominal value may be regarded as a reference value. Hence, the determined water band width D is smaller than the nominal value $D_{nom}$. Therefore, the intensity of a spectrum obtained by using the cuvette presently under consideration needs to be corrected. More specifically, in order for the spectrum to resemble a spectrum obtained from a cuvette with a pathlength corresponding to the nominal water band width $D_{nom}$, the background corrected intensity $C_n$ needs to be multiplied by an intensity correction factor Q which is larger than 1.

As indicated above, it may be established empirically that the pathlength deviation of the cuvette is approximately linearly related to the width of the water band D. In more detail, by representing the deviation of D from the nominal value Dnom by the quotient $D/D_{nom}$, it may be established that the following relation approximately holds:

$$a \cdot (D/D_{nom}-1)=1/Q-1,$$

where the deviation from the nominal pathlength is described by the reciprocal factor $1/Q$ (see below) and where a is a dimensionless constant. In fact, Q describes the intensity correction factor which consequently may be expressed as $$Q=1/(a \cdot (D/D_{nom}-1)+1)$$

The value of a may be determined empirically. In the present example, $a=1.5$.

It is stressed that in the present example, it is the reciprocal value of the intensity correction factor Q which is linearly correlated to the water band width D and, moreover, Q is related to the pathlength deviation. In more detail, the relation between Q and the pathlength may be described as follows. If the pathlength deviation is denoted by d and describes the deviation from a nominal value $L_{nom}$, the relation $L_{current}=L_{nom}+d$ is found. The nominal value $L_{nom}$ may be fixed from calculating an average pathlength for a plurality of cuvettes, but other methods of fixing the nominal value are equally conceivable. $L_{current}$ is a current pathlength measured by the spectrometer. It is noted that if there is no deviation from the nominal value, i.e. if $d=0$, then $L_{current}=L_{nom}$. According to the Beer-Lambert law, the intensity of a spectrum measured with the nominal pathlength $L_{nom}$ is $A_{nom}=\epsilon \cdot c \cdot L_{nom}$. Moreover, the intensity of a spectrum measured with the current pathlength $L_{current}$ is $A_{current}=\epsilon \cdot c \cdot L_{current}=\epsilon \cdot c \cdot (L_{nom}+d)$. Hence, it follows that $A_{nom}/A_{current}=L_{nom}/L_{current}$ or, equivalently, $A_{nom}=A_{current} \cdot L_{nom}/(L_{nom}+d)$. In order to convert the spectrum back to an intensity corresponding to the nominal pathlength, i.e. $A_{nom}$, the spectrum has to be multiplied by the factor $Q=L_{nom}/(L_{nom}+d)$.

Thus, by expressing the inverse Q-factor in two different ways, based on the formulas above, there is found a linear relation between the pathlength deviation d and the water-band width D. One way of verifying this relation is to measure the water band widths of a plurality of cuvettes having different pathlengths, and then to correlate these to the pathlengths as predicted by the method using a standardization sample. In order to establish the relation, a best-fit approximation scheme may be utilized. For instance, linear regression may be used. The error in the approximate linear relation may be as low as 0.1 percent, which is sufficiently accurate for a large number of spectral analyses within the food industry.

To reiterate, in the present example the intensity correction factor Q may be calculated by using the equation for Q in terms of a, D and $D_{nom}$ given above (Box 780). Thus, from to this formula spectra collected at slightly different pathlengths may be normalized with respect to a nominal pathlength. It is noted that if $D=D_{nom}$ the correction factor becomes $Q=1$ and no correction is needed. In the present example the correction factor becomes $$Q=1/(1.5 \cdot (101.12/105.31-1)+1) \approx 1.063.$$

This intensity correction factor Q is then applied to subsequent intensity spectra measured with the cuvette under consideration, e.g. when spectral analyses are performed on milk or wine. The intensity correction factor Q may be recalculated when a set of criteria is fulfilled. One such criterion may be that specific time intervals have passed. Q may be recalculated at regular time intervals. Typical time intervals may be anything between one hour and three hours, but clearly other time intervals are equally conceivable. The recalculated Q replaces the previously calculated factor. Another criterion may be that the calibration of the spectrometer becomes unreliable due to some control parameters of the spectrometer being outside an acceptable range of parameters.

It is understood that the intensity correction factor may be calculated by other means. Thus, the pathlength correction, and hence the intensity correction, is continuously updated to reflect the current state of the cuvette. Due to the continuous updating of Q, a degradation of the calcium fluoride comprised in the cuvette will be left essentially unnoticed by a user of the spectrometer.

In addition, as seen from the spectrometer, the correction will bring different cuvettes into the same state, irrespective of differences in their pathlengths.

Incidentally, it is noted that the method described above may be used for detecting air which is present in the cuvette comprising a sample, in particular a liquid sample, such as water presently under consideration. When a small air bubble is present in the cuvette, the water appears to be diluted, implying that the pathlength and the width of the water band appear smaller. Thus, a water band width smaller than a threshold value, may be an indication of air in the cuvette. Indeed, the signs of air in the cuvette are different than normal wear of the cuvette, since cuvette wear is characterized by an increasing water band width.

The invention has mainly been described above with reference to a few embodiments. However, as is readily appreciated by a person skilled in the art, other embodiments than the ones disclosed above are equally possible within the scope of the invention, as defined by the appended patent claims.

The invention claimed is:

1. A method of determining a pathlength deviation of a sample, the method comprising:
   exposing the sample to electromagnetic radiation at a plurality of wavenumbers;
   first determining electromagnetic absorption in the sample at the plurality of wavenumbers;
   second determining a first wavenumber associated with a first absorption level of an absorption band and a second wavenumber associated with a second absorption level of the absorption band, the second absorption level being equal to the first determining, the second wavenumber being different from the first wavenumber;
   third determining a difference between the first wavenumber and the second wavenumber;
   obtaining a nominal value representing a reference value of the width of the absorption band; and
   fourth determining the pathlength deviation based on the difference determined in the third determining and on the nominal value.

2. The method according to claim 1, wherein the electromagnetic radiation is infrared radiation.

3. The method according to claim 1, wherein the first determining determines the electromagnetic absorption using Fourier transform spectroscopy.

4. The method according to claim 1, wherein the first wavenumber and the second wavenumber correspond to positions on slopes of an electromagnetic radiation absorption band of water.

5. The method according to claim 1, further comprising:
   estimating a background spectrum by determining a third wavenumber associated with a third absorption level and a fourth wavenumber associated with a fourth absorption level, the third absorption level and the fourth absorption level being levels in a region at which the electromagnetic absorption is lower than the first absorption level and the second absorption level.

6. The method according to claim 5, wherein the estimating includes estimating the background spectrum as a polynomial of order N based on the third wavenumber and the fourth wavenumber and the third absorption level and the fourth absorption level.

7. The method according to claim 6, wherein the order N of the polynomial is two.

8. The method according to claim 1, wherein the fourth determining the pathlength deviation includes determining the pathlength deviation based on a linear relationship between the pathlength deviation and the difference determined in the third determining.

9. The method according to claim 1, further comprising:
   detecting air in the sample based on the pathlength deviation.

10. The method according to claim 1, further comprising:
    calibrating a spectrometer based on the pathlength deviation.

11. An apparatus configured to determine a pathlength deviation of a sample, the apparatus comprising:
    a radiation device configured to radiate electromagnetic radiation towards the sample at a plurality of wavenumbers; and
    a measuring device configured to,
        determine electromagnetic absorption in the sample at the plurality of wavenumbers,
        determine a first wavenumber associated with a first absorption level of an absorption band and a second wavenumber associated with a second absorption level of the absorption band, the second wavenumber being different from the first wavenumber and the first absorption level being the same as the second absorption level,
        determine a difference between the first wavenumber and the second wavenumber, and
        determine the pathlength deviation based on the difference and on a nominal value representing a reference value of a width of the absorption band.

12. The apparatus according to claim 11, wherein the electromagnetic radiation is infrared radiation.

13. The apparatus according to claim 11, wherein the measuring device is configured to determine the electromagnetic absorption using Fourier transform spectroscopy.

14. The apparatus according to claim 11, wherein the first wavenumber and the second wavenumber correspond to positions on slopes of an electromagnetic radiation absorption band of water.

15. A method of determining a pathlength deviation of a sample in a spectrometer, the method comprising:
    transmitting electromagnetic radiation from a radiation device towards the sample;
    first determining an electromagnetic radiation absorption spectrum of the sample;
    second determining an electromagnetic radiation absorption band within the electromagnetic radiation absorption spectrum;
    third determining a width of the electromagnetic radiation absorption band; and
    fourth determining the pathlength deviation based on the width of the electromagnetic radiation absorption band and on a nominal value representing a reference value of a width of the electromagnetic radiation absorption band.

16. The method according to claim 15, wherein the first determining the electromagnetic radiation absorption spectrum comprises:
   estimating background spectrum of the spectrometer based on a region at which the electromagnetic radiation absorption is lower than a region where the electromagnetic radiation absorption band of the sample is determined; and
   determining the electromagnetic radiation absorption spectrum by eliminating the background spectrum therefrom.

17. The method according to claim 15, wherein the first determining determines the electromagnetic radiation absorption spectrum based on a plurality of wavenumbers, and the second determining the electromagnetic radiation absorption band comprises:
   determining a first wavenumber associated with a first absorption level and a second wavenumber associated with a second absorption level among the plurality of wavenumbers; and
   calculating a difference between the first wavenumber and the second wavenumber, the first wavenumber and the second wavenumber corresponding to positions on slopes of the electromagnetic radiation absorption band.

18. The method according to claim 15, further comprising:
   calibrating the spectrometer based on the pathlength deviation.

* * * * *